US00PP11145P

United States Patent [19]

van Andel

[11] Patent Number: Plant 11,145

[45] Date of Patent: Dec. 7, 1999

[54] ALSTROEMERIA PLANT NAMED 'STAPRIPAL'

[75] Inventor: Jacob van Andel, Aalsmeer, Netherlands

[73] Assignee: Van Staaveren B.V., Aalsmeer, Netherlands

[21] Appl. No.: 09/021,510

[22] Filed: Feb. 10, 1998

[51] Int. Cl.[6] ..... A01H 5/00

[52] U.S. Cl. ..... Plt./309

[58] Field of Search ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is the result of a cross between two unnamed, undistributed varieties identified as 91D174-1, the seed parent, and 86G713-1, the pollen parent. The varietal denomination of the new variety is 'Stapripal'.

The first act of asexual reproduction of 'Stapripal' was in Aalsmeer, The Netherlands, by propagation by dividing the rhizomes and tissue culture. Asexual reproduction by dividing rhizomes through successive generations in Aalsmeer, The Netherlands, has demonstrated that the combination of characteristics as herein disclosed for 'Stapripal' are firmly fixed and retained through successive generations.

SUMMARY OF THE INVENTION

The new variety of Alstroemeria, 'Stapripal', produces long lasting flowers of unusual coloration, as described herein.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid plants about one year old as observed in a greenhouse in Aalsmeer, The Netherlands in the month of October. Color designations indicated are in accordance with The Royal Horticultural Society Colour Chart by color plate designations.

'Stapripal' has not been observed under all possible environmental conditions. Phenotypic expression may vary with variations in environment such as temperature, light intensity, day length and growing and cultural conditions.

Botanical classification:
- *Family.*—Amaryllidaceae.
- *Genus.*—Alstroemeria sp.
- *Commercial.*—Alstroemeria hybrid.

Origin: Seedling.

PLANT

Form: Bush, useful as pot plant or garden decoration.
Shape: Upright.
Height: About 22 to 45 cm.

Branching characteristics: Flowering stems do not branch.
Blooming habit:
- *Recurrent.*—From April up to and including October in the Netherlands.

Disease resistance: Unknown.
Foliage:
- *Quantity.*—Abundant.
- *Number of leaves.*—About 25 to 30.
- *Size of leaf.*—Length: About 3 to 10 cm. Width: About 1 to 2 cm.
- *Shape of leaf.*—Elliptic.
- *Margin.*—Minutely crimped.
- *Texture.*—Glossy.
- *Color.*—Upper side: Near 137A. Underside: Near 137C.
- *Venation.*—Curved.
- *Rhizomes.*—Color: Near 155D. Size: About 10 to 25 cm.

FLOWER

Size (when first anthers release pollen):
- *Diameter.*—About 5 to 6 cm.
- *Depth.*—About 4 to 5 cm.

Borne: Singly.
Shape or form:
- *When bloom first opens.*—Cup.

When bloom matures: Cup.
Fragrance: None.
Lasting quality:
- *On plant.*—About 21 days.
- *As cut flower.*—About 14 days.

Tepals:
Discoloration after full bloom: No.
- *Number of tepals.*—About 6.
- *Arrangement.*—2 concentric circles of 3 tepals
- *Shape.*—Tepals, obovate; bloom — cup shaped.
- *Margin.*—Slightly serrated.
- *Apex.*—Pointed.
- *Size of bloom fully expanded.*—Diameter about 5 to 6 cm, depth about 4 to 5 cm.
- *Texture.*—Soft.
- *Color.*—Outer tepals have a creamy, near 4D except at center, near 53B; the inner tepals also have a dark yellow center, near 13A; between the yellow center and a red tip there is a creamy spot near 4D; outer tepals have about 1 to 5 long stripes near 185A; inner tepals have about 20–30 stripes, near 185A.

Peduncle or flower stem: Length of pedicel about 2 to 3 cm, diameter about 0.5 cm; peduncle about 2 to 6 cm.
- *Color.*—Near 137 A.

*Strength.*—Strong.
*Number of blooms/stem.*—About 2 to 3, very small.
*Hairy.*—No.
Persistence: Flower does not hang on and dry.

BUD

Size:
*Diameter.*—About 0.5 to 1.0 cm.
*Depth or length.*—About 1 to 4 cm.
*Form or shape.*—Pear-shaped.
*Rate of opening.*—Fast.
*Color of tepals*
*When tepals begin to unfurl.*—Near 53B.

REPRODUCTIVE ORGANS

Stamen:
*Number.*—6.
*Arrangement.*—Around the style.
Anthers
*Size.*—0.5 to 1.0 cm.
*Color.*—Near 53B.
Filaments:
*Length.*—5 cm.
*Color.*—Near 53C.
Pollen:
*Color.*—Near 53B.
Pistils:
*Styles.*—Length about 4 to 6 cm.
*Color.*—Near 53C.
Stigmas:
*Color.*—Near 53D.

FRUIT

Fertile: Yes.
Shape: Round.
Color at maturity: Near 164 A.

I claim:

1. A new Alstroemeria plant of the variety substantially as herein shown and described.

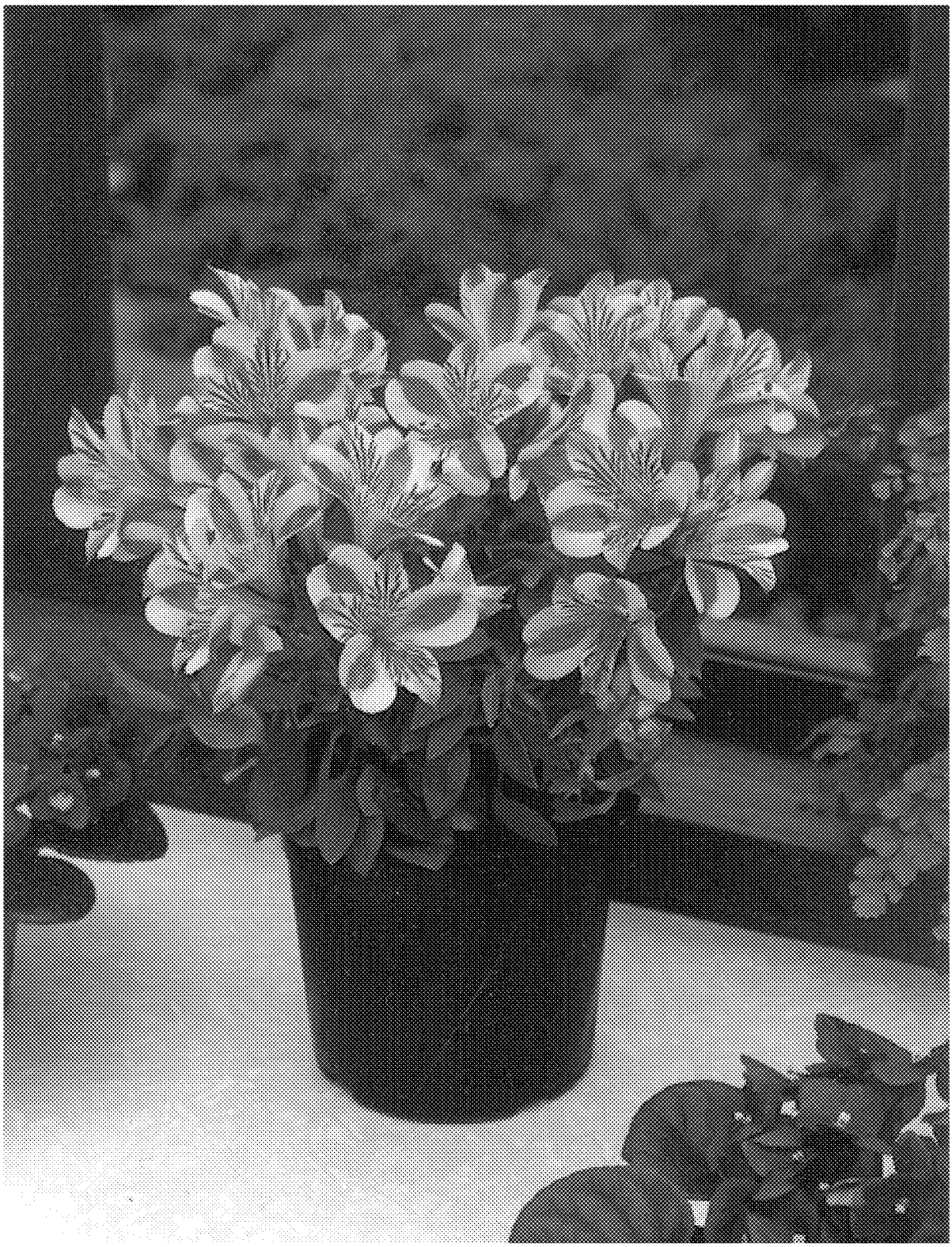

* * * * *